(12) United States Patent
Lee et al.

(10) Patent No.: US 6,547,899 B2
(45) Date of Patent: Apr. 15, 2003

(54) SYNTHESIS OF FINE-GRAINED TATB

(75) Inventors: Kien-Yin Lee, Santa Fe, NM (US); James E. Kennedy, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 174 days.

(21) Appl. No.: 09/811,044

(22) Filed: Mar. 15, 2001

(65) Prior Publication Data

US 2002/0129880 A1 Sep. 19, 2002

(51) Int. Cl.$^7$ ............................................. C06B 25/04
(52) U.S. Cl. ....................................... 149/105; 564/406
(58) Field of Search ........................... 149/105; 564/406

(56) References Cited

U.S. PATENT DOCUMENTS

| | | | | |
|---|---|---|---|---|
| 4,032,377 A | * | 6/1977 | Benziger | 149/105 |
| 4,248,798 A | * | 2/1981 | Atkins et al. | 564/441 |
| 4,481,371 A | * | 11/1984 | Benziger | 564/406 |
| 4,952,733 A | * | 8/1990 | Ott et al. | 564/406 |
| 5,569,783 A | * | 10/1996 | Mitchell et al. | 564/395 |
| 5,633,406 A | * | 5/1997 | Mitchell et al. | 564/395 |
| 6,069,277 A | * | 5/2000 | Mitchell et al. | 564/395 |
| 6,225,503 B1 | * | 5/2001 | Rigdon et al. | 564/441 |

OTHER PUBLICATIONS

J. Bremser et al., Journal of Energetic Materials, 1999, vol. 17 (2–3) pp 279–296. No month available.*
J. Bremser et al., International Annual Conference if ICT, (1998), 29$^{th}$ (Energetic Materials), pp. 13.1—13.13. No month available.*
K.-Y. Lee et al., International Annual Conference if ICT (1998), 29th (Energetic Materials), 177.1—177.14. No month available.*

* cited by examiner

Primary Examiner—John Hardee
(74) Attorney, Agent, or Firm—Samuel M. Freund

(57) ABSTRACT

A method for producing fine-grained triamino-trinitrobenzene (TATB) powders having improved detonation-spreading performance and hence increased shock sensitivity when compared with that for ultrafine TATB is described. A single-step, sonochemical amination of trichloro-trinitrobenzene using ammonium hydroxide solution in a sealed vessel yields TATB having approximately 6 μm median particle diameter and increased shock sensitivity.

8 Claims, 4 Drawing Sheets

SYNTHESIS OF FINE-GRAINED TATB

STATEMENT REGARDING FEDERAL RIGHTS

This invention was made with government support under Contract No. W7405-ENG-36 awarded by the U.S. Department of Energy to The Regents of The University of California. The government has certain rights in the invention.

FIELD OF THE INVENTION

The present invention relates generally to the synthesis of the insensitive high-explosive triaminotrinitrobenzene. (TATB) and, more particularly, to the synthesis of ultrafine TATB by sonochemical amination.

BACKGROUND OF THE INVENTION

The compound 1,3,5-triamino-2,4,6-trinitrobenzene (TATB) is an explosive having a high melting point and thermal stability that has been applied in situations where insensitivity to impact hazards is important. In the past, production-grade TATB was prepared by amination of 1,3,5-trichloro-2,4,6-trinitrobenzene (TCTNB) in toluene with anhydrous ammonia gas in a pressurized reactor. TATB thus produced is suitable for most applications requiring a particle size ranging from 30–60 $\mu$m. However, for applications requiring higher sensitivity to shock initiation, fine-grained TATB is desirable. Ultrafine TATB is generally considered to be TATB having a particle size under 10 $\mu$m. Unfortunately, the processes involved for the production of such ultrafine TATB (UF-TATB) are complicated and time consuming.

Ultrasound includes sound frequencies beyond human hearing; that is, above 16 kHz. When ultrasound is applied to liquids of either a homogeneous or heterogeneous reaction system, acoustic cavitation results. Rate enhancement of chemical reactions accompanied by higher production yields has been demonstrated under the influence of ultrasonic irradiation (ultrasonication).

In "Synthesis And Characterization Of Sonochemically Aminated 1,3,5-Triamino-2,4,6-Trinitrobenzene" by Julie Bremser et al., J. Energetic. Materials 17, 297 (1999), the preparation of TATB from TCTNB in toluene by amination with ammonium hydroxide solution under the influence of ultrasonic irradiation is described. The room-temperature reaction was initiated by immersing the sonicator horn of an ultrasonic liquid processor operating at 20 kHz into a vessel containing a two-phase solution of TCTNB in toluene and ammonium hydroxide. A piece of aluminum foil was used to cover the vessel in order to avoid the escape of a significant amount of ammonia gas. After 40 min. of sonication, the resulting emulsion was allowed to stand overnight at ambient temperature. The TATB precipitate was collected by filtration, washed sequentially with hot water, toluene and acetone, and dried at 98° C. in a vacuum oven overnight. Although the arithmetic median diameter of the TATB particles produced by this method was approximately 15 $\mu$m, the TATB was found to be slightly more sensitive to shock initiation than the approximately 5 $\mu$m median diameter micronized (fluid energy mill) UF-TATB prepared using established methods.

Accordingly, it is an object of the present invention to provide a method for preparing TATB having improved sensitivity to shock initiation over that for ultrafine TATB prepared by other methods.

Additional objects, advantages and novel features of the invention will be set forth, in part, in the description that follows, and, in part, will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects of the present invention, and in accordance with its purposes, as embodied and broadly described herein, the method for producing triamino-trinitrobenzene hereof includes ultrasonically mixing a solution of trichloro-trinitrobenzene in a solvent therefor and a solution of ammonium hydroxide in a cooled, sealed vessel such that an emulsion of triaminotrinitrobenzene is formed; and separating the triamino-trinitrobenzene from the emulsion.

It is preferred that the solvent for trichloro-trinitrobenzene is toluene.

Preferably, the solution of trichloro-trinitrobenzene and the solution of ammonium hydroxide are maintained at between 1° C. and 15° C. during the step of ultrasonically mixing the solutions.

Benefits and advantages of the present invention include the single-step production of fine-grained triamino-trinitrobenzene (TATB) powders having improved detonation-spreading performance and hence increased shock sensitivity when compared with that for ultrafine TATB (UF-TATB).

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 2a is a scanning electron micrograph of UF-TATB, while

DETAILED DESCRIPTION

Figure 1:
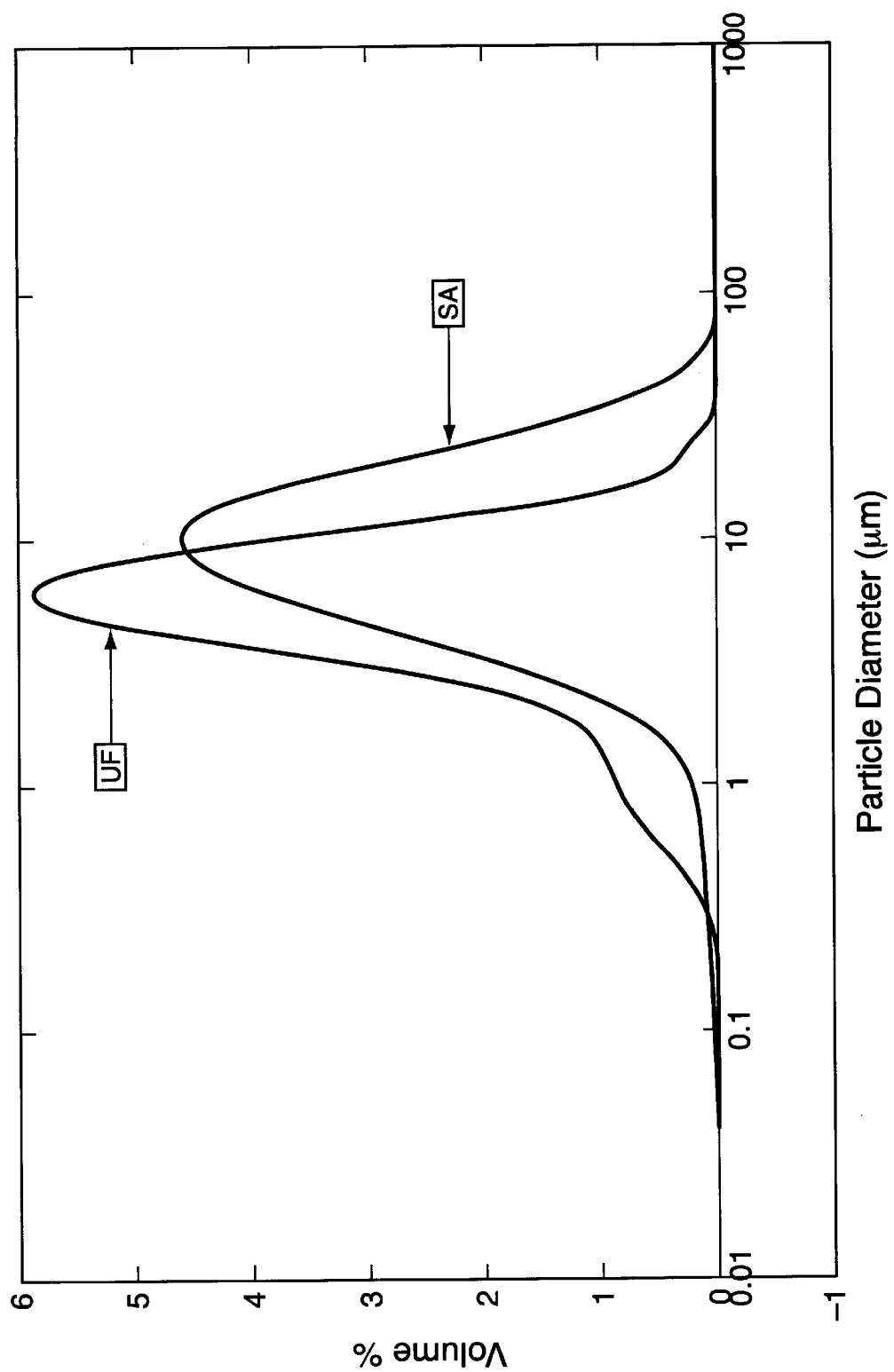
FIG. 1 is a graph of the volume percent for sonochemically aminated TATB (SA-TATB) and ultrafine TATB (UF-TATB) as a function of particle diameter and illustrates the particle size distributions for these two materials.

Briefly, the present invention includes the direct preparation of fine TATB powder using ammonium hydroxide solution and ultrasonic irradiation rather than anhydrous ammonia gas for the amination of TCTNB, since ultrasound generates extremely fine emulsions from mixtures of immiscible liquids.

Reference will now be made in detail to the present preferred embodiments of the invention which are illustrated in the accompanying drawings. A solution of TCTNB in toluene is added to an ammonium hydroxide solution in an air-sealed sonication reactor having a sonicator horn powered by a 20 kHz, variable-amplitude power supply output (275–330 W). The horn is disposed below the liquid level. The reactor is placed in a circulating bath at between 1° C. and 15° C. and the liquids sonochemically aminated between 10 min and 40 min. The resulting TATB was collected by filtration, washed sequentially with water, toluene and acetone, and dried in an oven. Particle-size analysis of aqueous TATB suspensions was performed using a particle sizer.

Having generally described the present invention, the following EXAMPLES provide additional detail.

EXAMPLE 1

To the air-sealed sonication reactor containing 25 ml of 30% aqueous ammonium hydroxide ($NH_4OH$) was added 15 ml of TCTNB (2.08 g of TCTNB, 85% purity) in toluene. The reactor was then sealed with the sonicator horn (0.5 in. probe) immersed in the liquid. The entire reactor was then immersed in a circulating bath at 1° C. With the sonicator power set at 330 W, the amination reaction was started. After 20 min. of sonication, the reaction was stopped and the sonicator allowed to warm to ambient temperature. The reaction mixture was then poured into a beaker, and the resulting TATB was collected by filtration using a membrane filter paper, washed sequentially with water, toluene and acetone, and dried in an oven at 98° C. The particle median diameter of the TATB was measured to be 4.90 μm.

EXAMPLE 2

To the air-sealed sonication reactor containing 15 ml of a stock solution of TCTNB (20.8 g of TCTNB in 140 ml of toluene which yields 150 ml of solution) was added 25 ml of 30% aqueous ammonium hydroxide. The reactor was then sealed with the sonicator horn (0.5 in. probe) immersed in the liquid. The entire reactor was then immersed in a circulating bath at 10° C. With the sonicator power set at 275 W, the amination reaction was started. After 20 min. of sonication, the reaction was stopped and the sonicator allowed to warm to ambient temperature. The reaction mixture was then poured into a beaker, and the resulting TATB was collected by filtration using a membrane filter paper, washed sequentially with water, toluene and acetone, and dried in an oven at 98° C. The particle median diameter of the TATB was measured to be 5.29 μm.

Figure 2A:
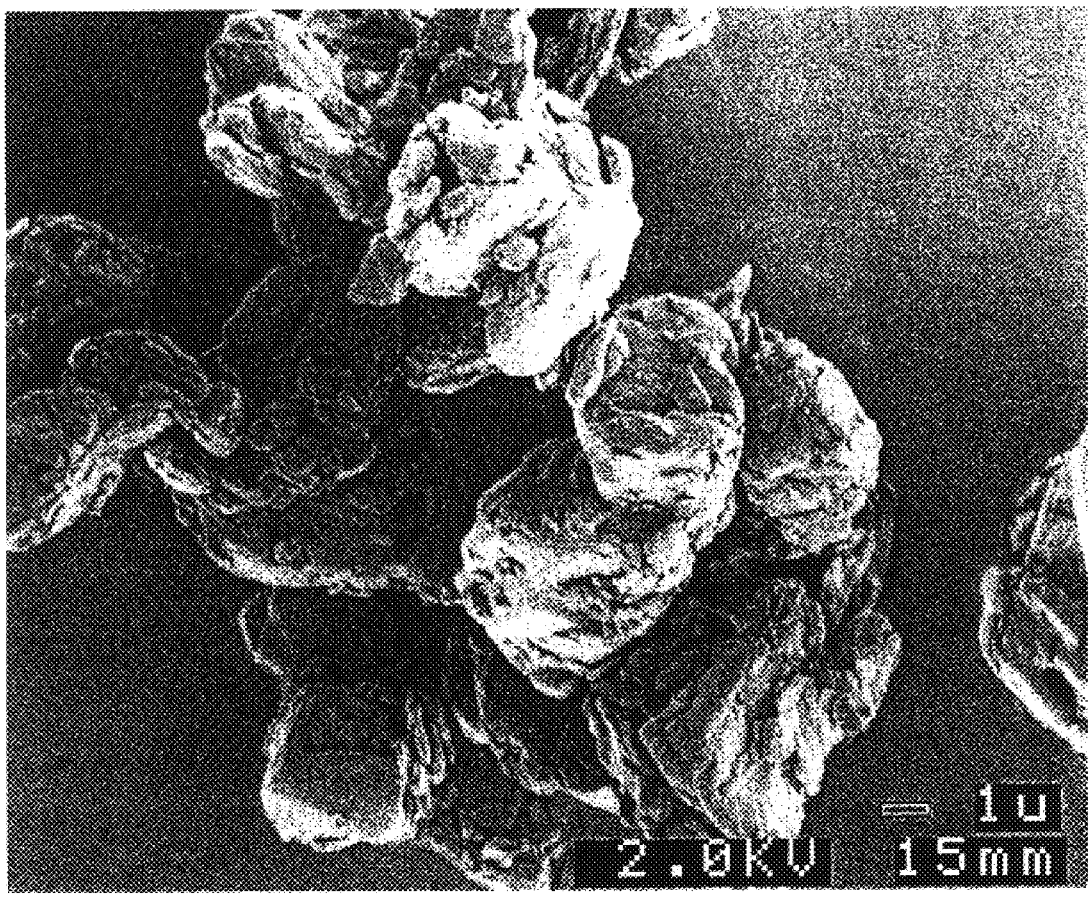
Figure 2B:
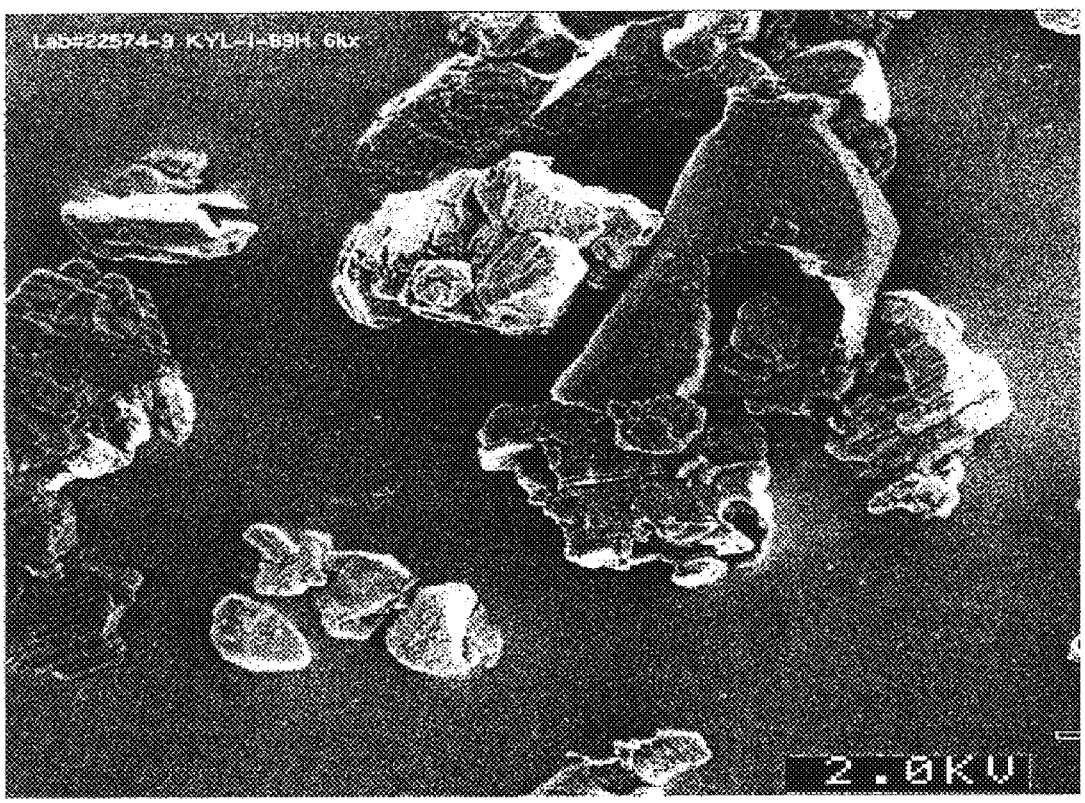
FIG. 2b is a scanning electron micrograph for SA-TATB.
Figure 3:
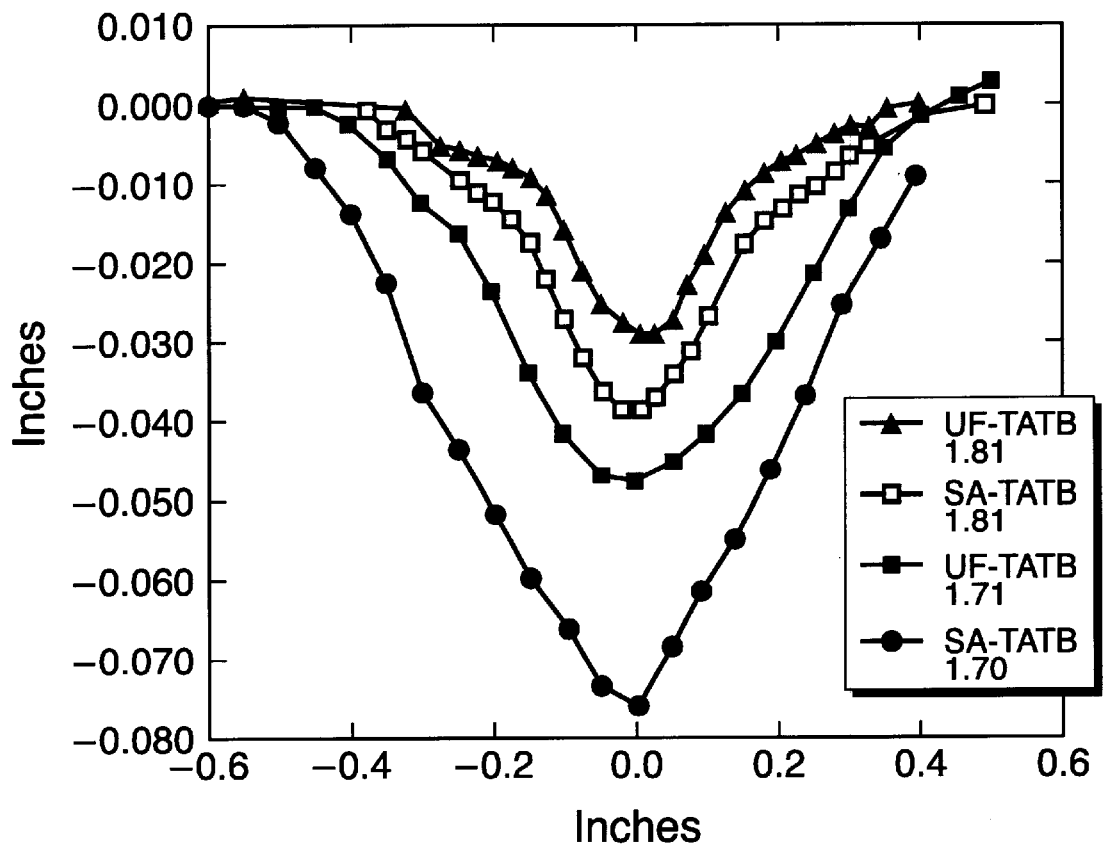
FIG. 3 is a graph of the dent profiles for UF-TATB and SA-TATB for two compacted densities, deeper dents indicating better detonation spreading.

Turning now to FIG. 1, a graph of the particle size distributions of both UF-TATB and SA-TATB are displayed as a function of particle diameter. From this graph, the median diameters of the two TATB powders are each determined to be approximately 6 μm. FIG. 2 shows the surface structure for TATB powders visualized using scanning electron microscopy. Samples were gold-coated for examination at room temperature. FIG. 2a shows the micrograph of UF-TATB, while FIG. 2b shows that for SA-TATB, both taken at 2 kV.

The Floret test (called the detonation-spreading spot-size test in "Detonation Spreading In Fine TATBs" by J. E. Kennedy et al., Proceedings, 24th International Pyrotechnics Seminar, Monterey, Calif., July, 1998, IIT Research Institute, pp. 743–748) is a means for ranking the shock sensitivity of fine TATB powders using a small quantity of powder. See also, "Synthesis, Detonation Spreading And Reaction Rate Modeling Of Fine TATB" by Kien-Yin Lee et al., 11th International Detonation Symposium, Aug. 31 through Sep. 4, 1998, Snowmass Conference Center, Snowmass Village, Colo. 81615, pp. 362, released in August, 2000. The test involves the impact of a thin pellet of pressed TATB by an explosively driven stainless-steel flyer plate that is much smaller in diameter than the explosive pellet. In insensitive high explosives, detonation initiated over a small area may not spread throughout the entire diameter of the pellet. The degree of detonation spreading is determined by measurement of the dent pattern produced on a copper plate upon which the TATB pellet rests. Floret testing was performed at room temperature and a strong dependence of the detonation spreading behavior on pellet density was observed. FIG. 8 shows that SA-TATB displays better detonation spreading performance than UF-TATB. In earlier work (see, e.g., Julie Bremser et al., supra) detonation spreading of FP-TATB was found to be slightly better than that for UF-TATB at about 1.81 $g/cm^3$, but the improvement was not significant. Since the detonation spreading behavior of fine TATB is much better at low density, tests were performed at 1.70 $g/cm^3$ with SA-TATB. Results confirmed the improved detonation spreading, showing that SA-TATB performs much better than UF-TATB at this lower density.

In conclusion, finer TATB materials having greater shock sensitivity (as measured by detonation-spreading behavior) than UF-TATB at the same density can be produced using a simple one-step method.

The foregoing description of the invention has been presented for purposes of illustration and description and is not intended to be exhaustive or to limit the invention to the precise form disclosed, and obviously many modifications and variations are possible in light of the above teaching. For example, The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for producing triamino-trinitrobenzene comprising the steps of ultrasonically mixing a solution of trichloro-trinitrobenzene in a solvent therefor and a solution of ammonium hydroxide in a cooled, sealed reactor such that a suspension of triamino-trinitrobenzene is formed; and separating the triamino-trinitrobenzene from the suspension.

2. The method as described in claim 1 wherein the solvent for trichlorotrinitrobenzene is toluene.

3. The method as described in claim 1 wherein said step of separating the triamino-trinitrobenzene from the emulsion is achieved by filtration.

4. The method as described in claim 1 wherein the cooled reactor is maintained between 1° C. and 15° C. during said step of ultrasonically mixing the solution of trichloro-trinitrobenzene in a solvent therefor and the solution of ammonium hydroxide.

5. The method as described in claim 1 wherein the solution of ammonium hydroxide is an aqueous solution of ammonium hydroxide.

6. The method as described in claim 1 wherein said step of ultrasonically mixing the solution of trichloro-trinitrobenzene in a solvent therefor and the solution of ammonium hydroxide is performed at 20 kHz and at an ultrasonic power level of between 275 and 330 W.

7. The method as described in claim 1 further comprising the steps of washing and drying the separated triamino-trinitrobenzene.

8. The method as described in claim 1 wherein said step of ultrasonically mixing a solution of trichloro-trinitrobenzene in a solvent therefor and a solution of ammonium hydroxide is performed for a time period between 10 and 40 min.

* * * * *